United States Patent
Andes et al.

[11] Patent Number: 5,972,098
[45] Date of Patent: Oct. 26, 1999

[54] TITANATE-CONTAINING PEARLESCENT PIGMENTS

[75] Inventors: Stefanie Andes, Maintal; Sabine Hock, Schaafheim; Günter Brenner, Griesheim; Dieter Brückner, Darmstadt; Andrea Heyland, Ober-Kainsbach; Matthias Kuntz, Seeheim; Karl Osterried, Dieburg; Gerhard Pfaff, Münster; Michael Schmelz, Kriftel, all of Germany

[73] Assignee: Merck Patent GmbH, Germany

[21] Appl. No.: 08/983,347

[22] PCT Filed: Apr. 26, 1997

[86] PCT No.: PCT/EP97/02168

§ 371 Date: Jan. 9, 1998

§ 102(e) Date: Jan. 9, 1998

[87] PCT Pub. No.: WO97/43348

PCT Pub. Date: Nov. 20, 1997

[30] Foreign Application Priority Data

May 9, 1996 [DE] Germany ............ 196 18 563

[51] Int. Cl.⁶ .................................................. C09C 1/36
[52] U.S. Cl. ................. 106/436; 106/415; 106/418; 106/437; 106/439; 428/402; 428/403; 428/404
[58] Field of Search .............................. 106/415, 418, 106/437, 439; 428/403, 404, 402

[56] References Cited

U.S. PATENT DOCUMENTS

| | | | |
|---|---|---|---|
| 3,395,203 | 7/1968 | Morita et al. | 264/141 |
| 3,767,443 | 10/1973 | Clark et al. | 106/415 |
| 4,344,987 | 8/1982 | Ostertag et al. | 427/213 |
| 4,744,832 | 5/1988 | Franz et al. | 106/418 |
| 5,009,711 | 4/1991 | Emmert et al. | 106/415 |

FOREIGN PATENT DOCUMENTS

| | | |
|---|---|---|
| 045 851 | 2/1982 | European Pat. Off. . |
| 211 351 | 2/1987 | European Pat. Off. . |
| 307 747 | 3/1989 | European Pat. Off. . |
| 1 273 230 | 2/1962 | France . |

OTHER PUBLICATIONS

Derwent abstract 87–039671 of JP 61 295 234 A, Dec. 1986.
Derwent Publications, AN 87–039671 (Dec. 26, 1986).

*Primary Examiner*—Mark L. Bell
*Assistant Examiner*—Scott L. Hertzog
*Attorney, Agent, or Firm*—Millen, White, Zelano & Branigan, P.C.

[57] ABSTRACT

Single-layer or multilayer titanate-containing pearlescent pigments comprising iron titanate and, if appropriate, titanium oxide and/or iron oxide, which is obtainable by solidification of an aqueous solution of a thermally hydrolysable titanium compound on a continuous belt, detachment of the layer formed, coating of the resulting titanium dioxide platelets, after or without intermediate drying, with iron oxide in a wet process, and drying and calcining of the resulting material in an oxidizing or reducing gas atmosphere at not less than 500° C., the layer thicknesses of the titanium dioxide layer and iron dioxide layer being adjusted such that either the stoichiometric ratio between iron oxide and titanium dioxide necessary for the formation of pseudo-brookite or ilmenite is obtained or an excess of iron oxide or titanium dioxide is present.

9 Claims, 1 Drawing Sheet

TITANATE-CONTAINING PEARLESCENT PIGMENTS

The invention relates to very thin pearlescent pigments based on plateletlike titanium dioxide coated with iron oxide.

Pearlescent (pearl lustre) pigments containing iron oxide have been described in several instances and have been successfully used for many years. Both pigments in which iron oxide is precipitated together with titanium dioxide onto the substrate and pigments in which the precipitations are carried out in succession are described. During subsequent calcining, iron oxide diffuses into the $TiO_2$ layer and pseudo-brookite ($Fe_2TiO_5$) is formed. Mica is used exclusively as the substrate.

U.S. Pat. No. 3,087,828 reports that gold-colored mica pigments which assume a reddish colour shade on calcining are obtained by deposition of an $Fe_2O_3$ layer onto a $TiO_2$ layer.

U.S. Pat. No. 3,874,890 describes a process for the preparation of gold-colored pearlescent pigments in which a mica pigment coated with $TiO_2$ and/or $ZrO_2$ is first coated with iron(II) hydroxide, which is then oxidized to $Fe_2O_3$.

U.S. Pat. No. 4,744,832 describes a pearlescent pigment based on plateletlike substrates, in particular mica, coated with metal oxides, the metal oxide layer comprising both titanium and iron and the pigment having a multilayer build-up, a layer of pseudo-brookite and an iron oxide layer following a first layer of $TiO_2$ in the rutile form.

Mica pigments are widely used in the printing and coating industry, in cosmetics and in plastics processing. They are distinguished by interference colors and a high gloss. However, mica pigments are unsuitable for the formation of extremely thin layers, because mica, as the substrate for the metal oxide layers of the pigment, already has a thickness of 200 to 1200 nm. Another disadvantage is that the thickness of the mica platelets within a certain fraction, which is determined by the platelet size, sometimes varies significantly around a mean value. Furthermore, mica is a naturally occurring mineral which is contaminated by foreign ions. Processing steps which are very expensive industrially and time-consuming are, moreover, necessary. These include, above all, grinding and grading.

Pearlescent pigments which are based on thick mica platelets and are covered with metal oxides have a significant scatter content because of the thickness of the edge, especially at finer particle size distributions below 20 $\mu$m.

Thin glass platelets which are obtained by milling a glass melt with subsequent grinding have been proposed as a substitute for mica. Interference pigments based on such materials indeed show color effects which are superior to those of conventional pigments based on mica. A disadvantage is, however, that the glass platelets have a very large average thickness of about 10–15 $\mu$m and a very wide thickness distribution (typically between 4 and 20 $\mu$m), while the thickness of interference pigments typically is not greater than 3 $\mu$m.

EP 0,384,596 describes a process in which hydrated alkali metal silicate is charged with a jet of air at temperatures of 480–500° C., bubbles with low wall thicknesses forming; the bubbles are then comminuted and plateletlike alkali metal silicate substrates having a thickness of less than 3 $\mu$m are obtained. However, the process is expensive and the thickness distribution of the resulting platelets is relatively wide.

DE 11 36 042 describes a continuous belt process for the preparation of plateletlike or spangle-like oxides or hydrated oxides of metals of group IV and V and of the iron group of the Periodic Table. In this process, if appropriate, a separating layer of, for example, silicone varnish is first applied to a continuous belt to facilitate later detachment of the metal oxide layer. A liquid film of a solution of a hydrolyzable compound of the metal to be converted into the desired oxide is then applied and the film is dried and then detached with a vibrating device. The layer thickness of the resulting platelets is stated as 0.2 to 2 $\mu$m, without concrete examples being given of this.

EP 0,240,952 and EP 0,236,952 have proposed a continuous belt process for the preparation of various plateletlike materials, including silicon dioxide, aluminium oxide and titanium dioxide. In this process, a thin liquid film of defined thickness of a precursor of the plateletlike material is applied to a smooth belt via a roller system; the film is dried and detached from the belt, plateletlike particles being formed. The particles are then calcined, if appropriate, ground and graded.

The thickness of the platelets obtained by the process described in EP 0 240 952 is relatively well-defined, since the film, for example, is applied very uniformly to the continuous belt via a roller system. The layer thickness of the platelets is stated as 0.3 to 3.0 $\mu$m in the examples. According to Example 1, a first roller is wetted with the precursor used by partly immersing this roller in a reservoir tank filled with the precursor. The film is transferred from this roller onto a second roller rotating in the same direction, which is in very close contact with the first. Finally, the film is rolled from the second roller onto the continuous belt.

However, disadvantages are the use of very expensive precursor materials and, in particular, the increased requirements on workplace safety which must be imposed when organometallic compounds are employed. Complete chemical conversion of the precursor into the desired material of the layer as a rule renders severe heating of the film and of the belt material necessary. In addition to the considerable thermal stressing of the belt material that occurs in this case, the high energy consumption and the limitation of the speed of the process also have very adverse effects on the profitability of the process.

WO 93/08 237 describes plateletlike pigments comprising a plateletlike matrix of silicon dioxide, which can comprise soluble or insoluble coloring agents and which is coated with one or more reflecting layers of metal oxides or metals. The plateletlike matrix is prepared by solidification of water-glass on a continuous belt.

DE 1 273 098 describes the preparation of a nacreous pigment by vapor deposition of ZnS, $MgF_2$, ZnO, $CaF_2$ and $TiO_2$ films onto a continuous belt. However, like the process described in U.S. Pat. No. 4,879,140, in which plateletlike pigments with Si and $SiO_2$ layers are obtained by plasma deposition from $SiH_4$ and $SiCl_4$, this process is associated with a very high expenditure on apparatus.

In spite of numerous attempts, it has not yet been possible to develop an economic process for the preparation of very thin plateletlike titanium dioxide pigments having a coating thickness of less than 500 nm.

SUMMARY OF THE INVENTION

An object of the invention is to provide a high-lustre titanium-containing pearlescent pigment with a coating thickness of less than 500 nm and a layer thickness tolerance of less than 10%.

This object is achieved according to the invention by a single-layer or multilayer pearlescent pigment comprising iron titanate and, if appropriate, titanium oxide and/or iron oxide, which is obtainable by solidification of an aqueous solution of a thermally hydrolysable titanium compound on a continuous belt, detachment of the layer formed, coating of the resulting titanium dioxide platelets, without intermediate drying, with iron oxide in a wet process, and drying and calcining of the resulting material in an oxidizing or reducing gas atmosphere at not less than 700° C.

The iron titanate comprises either pseudo-brookite ($Fe_2TiO_5$) or ilmenite ($FeTiO_3$). The aqueous solution of a thermally hydrolysable titanium compound for the preparation of the titanium dioxide platelets on the continuous belt is preferably an aqueous titanium tetrachloride solution. The concentration of the titanium salt in this solution is 7 to 30% by weight, preferably 8 to 15% by weight.

The pigments according to the invention are based on plateletlike titanium dioxide particles. These platelets have a thickness of between 10 nm and 500 nm, preferably between 40 and 150 nm. The extent in the other two dimensions is between 2 and 200 µm, and in particular between 5 and 50 µm.

The composition and the layer build-up of the pigment according to the invention depends on the thickness of the titanium dioxide platelets used as the substrate, the layer thickness of the iron oxide and titanium dioxide applied and the calcining conditions.

The iron oxide layer and the titanium dioxide layer are preferably applied to the titanium dioxide platelets by known processes of wet chemistry. Furthermore, the dried titanium dioxide platelets can also be coated by gas-phase coating in a fluidized bed reactor, it being possible for the processes proposed in EP 0 045 851 and EP 0 106 235 for the preparation of pearlescent pigments to be used accordingly.

In a first embodiment, the pigment comprises only iron titanate.

In a second embodiment, the pigment has two layers, the core being formed from plateletlike titanium dioxide and the top layer being formed from iron titanate.

In a third embodiment, the pigment has a three-layer build-up, a core of plateletlike titanium dioxide being followed by a layer of iron titanate and a top layer of iron oxide. In a particular embodiment, this pigment has an additional iron titanate layer and a titanium dioxide layer as the top layer.

This object is furthermore achieved according to the invention by a process for the preparation of a pigment according to the invention, the pigment comprising only iron titanate, in which an aqueous solution of a thermally hydrolyzable titanium compound is applied as a thin film to a continuous belt, the film thickness being adjusted such that the stoichiometric ratio between iron and titanium necessary for the formation of pseudo-brookite or ilmenite is established, the liquid film is solidified by drying, during which the titanium dioxide is developed from the solution by a chemical reaction, the layer formed is then detached from the belt and washed, the resulting titanium dioxide platelets are suspended in water, after or without intermediate drying, and coated with iron oxide, the layer thickness being adjusted such that the stoichiometric ratio between iron and titanium necessary for the formation of pseudo-brookite or ilmenite is obtained, and the coated particles are separated off from the aqueous suspension and dried and calcined in an oxidizing or reducing atmosphere at not less than 500° C.

This object is furthermore achieved according to the invention by a process for the preparation of a pigment according to the invention, the pigment being formed from a core of plateletlike titanium dioxide and a top layer of iron titanate, in which an aqueous solution of a thermally hydrolyzable titanium compound is applied as a thin film to a continuous belt, the film thickness being adjusted such that an excess of titanium dioxide is present for the formation of both ilmenite and pseudo-brookite, the liquid film is solidified by drying, during which the titanium dioxide is developed from the solution by a chemical reaction, the layer formed is then detached from the belt and washed, the resulting titanium dioxide particles are suspended in water, after or without intermediate drying, and coated with iron oxide, the layer thickness being adjusted such that an excess of titanium dioxide is present for the formation of both ilmenite and pseudo-brookite, and the coated particles are separated off from the aqueous suspension and dried and calcined in an oxidizing or reducing atmosphere at not less than 500° C.

This object is furthermore achieved according to the invention by a process for the preparation of a pigment according to the invention, wherein the pigment has three layers and a core of plateletlike titanium dioxide is followed by a layer of iron titanate and a top layer of iron oxide, in which an aqueous solution of a thermally hydrolyzable titanium compound is applied as a thin film to a continuous belt, the film thickness being adjusted such that a layer thickness of the $TiO_2$ layer of at least 40 nm results, the liquid film is solidified by drying, during which the titanium dioxide is developed from the precursor by a chemical reaction, the layer formed is then detached from the belt and washed, the resulting titanium dioxide particles are suspended in water, after or without intermediate drying, and coated with iron oxide, the iron oxide precipitation being carried out such that a layer thickness of at least 20 nm results after the drying, and the coated particles are separated off from the aqueous suspension and dried and calcined in an oxidizing or reducing atmosphere at not less than 500° C.

In a particular embodiment, the pigment has an additional iron titanate layer and a top layer of titanium dioxide, in that a titanium dioxide layer is also precipitated onto the iron oxide layer, the titanium dioxide precipitation being carried out such that a layer thickness of at least 40 nm results after drying.

The invention furthermore relates to the use of the pigments according to the invention for pigmenting coatings, printing inks, plastics, cosmetics and glazing for ceramics and glass. They can also be employed here as mixtures with commercially available pigments, for example inorganic and organic absorption pigments, metal-effect pigments and LCP pigments.

The pigments according to the invention are prepared in a multi-stage process. In the first stage, the substrate is first prepared in the form of titanium dioxide platelets with the aid of a continuous belt. In a second stage, iron oxide is precipitated onto the substrate, a layer of titanium dioxide also being precipitated onto the iron oxide layer if appropriate. In a concluding stage, the pigment is calcined under oxidizing or reducing conditions, as a result of which the final layered structure of the pigment is formed.

Figure 1:
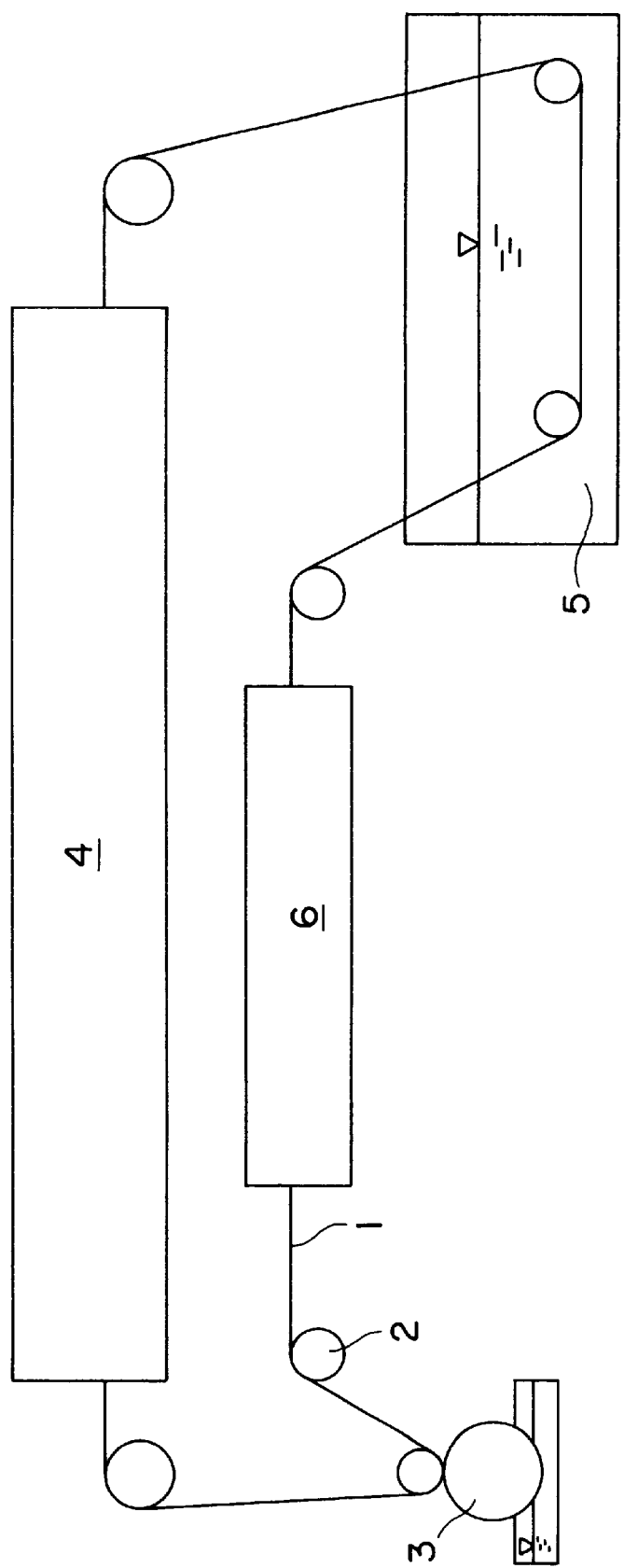
FIG. 1 shows the belt method of producing the instant particles.

The belt process will first be explained with the aid of FIG. 1.

The continuous belt 1, which is guided over a roller system 2, passes through an applicator 3, where it is coated with a thin film of the precursor. Roller applicators and flow units can be employed as suitable applicators. The belt speed is between 2 and 400 m/minute, preferably 5–200 m/minute.

In order to achieve uniform wetting of the belt of plastic, it is expedient to add to the coating solution a commercially available wetting agent or to activate the belt surface by flaming, corona treatment or ionization.

The coated belt then runs through a drying zone 4, in which the layer is dried at temperatures between 30 and 200° C. Commercially available infrared, ambient air jet and UV dryers, for example, can be employed as the dryer.

After passing through the drying zone, the belt is guided through the detachment baths 5 with a suitable detachment medium, for example completely desalinated water, where the dried layer is removed from the belt. The detachment operation is assisted here by additional devices, for example jets, branches or ultrasound.

The belt is dried in an after-dryer 6 before renewed coating.

The continuous belt should be made of a chemically stable and heat-resistant plastic in order to ensure an adequate service life and high drying temperatures. Materials such as polyethylene terephthalate (PET) or other polyesters and polyacrylates are suitable for this.

The film width is typically between a few centimeters up to several meters. The thickness is between 10 $\mu$m up to a few mm, these two parameters being optimized in respect of the particular requirements.

Further details of continuous belt processes are known from U.S. Pat. No. 3,138,475, EP 0 240 952 and WO 93/08 237.

The titanium dioxide platelets detached from the belt are coated with iron oxide by known processes in a second process stage without prior intermediate drying. The starting materials used here can be both iron(III) salts, such as is described, for example, in U.S. Pat. No. 3,087,828 and U.S. Pat. No. 3,087,829, and iron(III) salts, as described in U.S. Pat. No. 3,874,890, the coating of iron(II) hydroxide initially formed being oxidized to iron(III) oxide hydrate. Iron(III) salts are preferably used as starting materials. For this, an iron(III) chloride solution is metered into an aqueous suspension of the titanium dioxide platelets at a temperature of 60 to 90° C. and at a pH of 2.5 to 4.5. The pH is kept constant by simultaneously metering in 32% sodium hydroxide solution.

If appropriate, a titanium dioxide hydrate layer is then also precipitated onto the iron oxide hydrate layer by known processes. The process described in U.S. Pat. No. 3,553,001 is preferably used.

In this procedure, an aqueous titanium salt solution is slowly added to a suspension, heated to about 50–100° C., in particular 70–80° C., of the titanium dioxide platelets coated with iron oxide hydrate, and a largely constant pH of about 0.5–5, in particular about 1.5–2.5, is maintained by simultaneously metering in a base, such as, for example, aqueous ammonia solution or an aqueous alkali metal hydroxide solution. As soon as the desired layer thickness of the $TiO_2$ precipitate is reached, the addition of the titanium salt solution is stopped.

This process, which is also called the titration process, has the feature that an excess of titanium salt is avoided. This is achieved by a procedure in which only an amount per unit time such as is necessary for uniform coating with the hydrated $TiO_2$ and such as can be absorbed per unit time by the available surface of the particles to be coated is added to the hydrolysis. No hydrated titanium dioxide particles which are not precipitated on the surface to be coated are therefore formed. The amount of titanium salt added per minute here is of the order of about 0.01 to $2\times10^{-4}$ mol of titanium salt per square meter of surface to be covered.

In a third process stage, the titanium dioxide platelets coated with iron oxide hydrate and, if appropriate, additionally with titanium dioxide hydrate are calcined at 500 to 950° C., preferably at 800 to 900° C., under oxidizing or reducing conditions, after being separated off from the suspension, washed and dried. Under these conditions, iron diffuses into the $TiO_2$ layer, pseudo-brookite being formed in the presence of oxygen and ilmenite being formed in the presence of a reducing agent, for example hydrogen. With an appropriate choice of the layer thickness of iron oxide and titanium dioxide, a pigment which exclusively comprises iron titanate is obtained.

This is the case if the stoichiometric ratio between iron and titanium necessary for the formation of pseudo-brookite or ilmenite is established.

On the other hand, if the content of iron oxide is below the stoichiometric ratio, a pigment having a core of plateletlike titanium dioxide and a top layer of iron titanate is obtained.

If a 3-layer build-up of $TiO_2$/iron titanate/$Fe_2O_3$ or a 5-layer build-up of $TiO_2$/iron titanate/$Fe_2O_3$/iron titanate/$TiO_2$ of the pigment according to the invention is desired, both the titanium dioxide platelet and the iron oxide hydrate layer precipitated on and the titanium dioxide hydrate layer also precipitated on, if appropriate, must have certain minimum thicknesses.

Layer thicknesses of the titanium dioxide hydrate layer or of the titanium dioxide platelet of 40 to 200 nm and, in particular, of 40 to 150 nm are preferred.

However, in particular, the layer thickness of the $Fe_2O_3$ layer precipitated on is also essential for the 3- or 5-layer build-up. This should be high enough in each case such that, after the calcining and the formation of an intermediate layer of pseudo-brookite or ilmenite which takes place during this operation, a pure $Fe_2O_3$ layer of at least about 15 nm, and preferably layers with about 15 to about 50 nm, in particular those of about 20 to about 40 nm, is also present.

Further information on the preparation of a multilayer pigment can be found in U.S. Pat. No. 4,744,832.

It is furthermore possible to subject the pigments to after-coating or after-treatment which further increases the stability to light, weathering and chemicals or facilitates handling of the pigment, in particular incorporation into various media. Possible after-coating or after-treatment processes are, for example, those described in DE-C/A 22 15 191, DE-C/A 31 51 354, DE-C/A 32 35 017 or DE-OS 33 34 598. Owing to the fact that the properties of the pigments according to the invention are already very good without these additional measures, these substances which are also applied, if appropriate, make up only about 0–5, in particular 0–3% by weight of the total pigment.

The pigment according to the invention can also additionally be coated with sparingly soluble, firmly adhering inorganic or organic coloring agents. Color lakes, and in particular aluminium color lakes, are preferably used. For this, an aluminium hydroxide layer is precipitated on and is laked with a color lake in a second step. The process is described in more detail in DE 24 29 762 and DE 29 28 287.

Additional coating with complex salt pigments, in particular cyanoferrate complexes, such as, for example Prussian blue or Turnbull's blue, such as is described in EP 0 141 173 and DE 23 13 332, is also preferred.

The pigment according to the invention can also be coated with organic dyestuffs, and in particular with phthalocyanine or metal phthalocyanine and/or indanthrene dyestuffs, according to DE 40 09 567. For this, a suspension of the pigment in a solution of the dyestuff is prepared and this is then brought together with a solvent in which the dyestuff is sparingly soluble or insoluble.

Metal chalcogenides or metal hydrochalcogenides and carbon black can furthermore also be employed for an additional coating.

The pigment according to the invention represents the maximum ideal state which can be achieved in pearlescent pigments in respect of thickness, since it comprises only optically functional layers, and a carrier material which is otherwise customary, such as, for example, mica or glass platelets, which does not contribute towards the optical effect, is absent. As a result of the thickness of the mica, mica pigments have a thickness which is greater by a factor of up to 25 for the same thickness of the functional layers. Intrinsic advantages in respect of industrial applications which cannot be achieved by any other conventional pearlescent pigment result from this. For example, coatings can be applied in thinner layers and the amount of pigment needed can be reduced, because the pigments are more optically active due to the absence of the "filler" carrying material.

The examples described below are intended to illustrate the invention without limiting it.

EXAMPLES

Example 1

15 g of $TiO_2$ platelets (layer thickness about 60 nm) are suspended in 2000 ml of completely desalinated water (CDS water) and the suspension is heated to 75° C.

The pH of the suspension is adjusted to 3.0 with 10% hydrochloric acid. 610 g of an aqueous 10% $FeCl_3$ solution are now metered in at 75° C. in the course of 4 hours, the pH being kept constant by simultaneous addition of 32% sodium hydroxide solution. To bring the precipitation to completion, the mixture is subsequently stirred at 75° C. for a further 45 minutes.

The mixture is then allowed to cool to room temperature and the resulting red-brown pigment is filtered off, washed with CDS water until free from salts and dried at 100° C. Finally, it is calcined at 850° C. for 45 minutes. A copper-red pearlescent pigment of pseudo-brookite with a golden interference color is obtained.

Example 2

38 g of $TiO_2$ platelets are suspended in 2000 ml of CDS water and the suspension is heated to 75° C.

The pH of the suspension is adjusted to 3.0 with 10% hydrochloric acid. 770 g of an aqueous 10% $FeCl_3$ solution are now metered in at 75° C. in the course of 5 hours, while keeping the pH constant by simultaneous addition of 32% sodium hydroxide solution. To bring the precipitation to completion, the mixture is subsequently stirred at 75° C. for a further 45 minutes.

The mixture is then allowed to cool to room temperature and the resulting pigment is filtered off, washed with CDS water until free from salts and dried at 100° C. Finally, it is calcined at 850° C. for 45 minutes. A gold-colored pearlescent pigment which comprises 25% titanium dioxide and 75% pseudo-brookite is obtained.

Example 3

20 g of the dried pigment prepared in Example 2 are calcined in a tubular oven under forming gas ($N_2/H_2$=95/5) at 750° C. for 3 hours. A blue-black, lustrous pigment with an ilmenite structure is obtained.

Example 4

The dried pigment prepared in Example 2 is calcined in air at not less than 700° C. A red-brown pearlescent pigment which has a copper interference colour and comprises a titanium dioxide core, a pseudo-brookite layer and a haematite outer layer is obtained.

Example 5

30 g of $TiO_2$ platelets are suspended in 2000 ml of CDS water and the suspension is heated to 75° C.

The pH of the suspension is adjusted to 3.0 with 10% hydrochloric acid. 815 g of an aqueous 10% $FeCl_3$ solution are now metered in at 75° C. in the course of 5 hours, while keeping the pH constant by simultaneous addition of 32% sodium hydroxide solution. To bring the precipitation to completion, the mixture is subsequently stirred at 75° C. for a further 30 minutes.

120 ml of an aqueous $TiCl_4$ solution (400 g of $TiCl_4$/l) are now metered in over a period of 60 minutes. The pH is kept constant at 2.2 with 32% NaOH solution throughout the entire addition. When the addition has ended, the mixture is subsequently stirred at 75° C. for 30 minutes in order to bring the precipitation to completion.

The mixture is then allowed to cool to room temperature and the resulting pigment is filtered off, washed with CDS water until free from salts and dried at 110° C. Finally, it is calcined at 850° C. for 30 minutes. A gold-colored pearlescent pigment which has a reddish interference color and comprises a titanium dioxide core, a pseudo-brookite layer and a titanium dioxide outer layer is obtained.

We claim:

1. A single-layer or multilayer titanate-containing pearlescent pigment comprising iron titanate and optionally titanium oxide and/or iron oxide, which is obtained by solidification of an aqueous solution of a thermally hydrolyzable titanium compound on a continuous belt, detachment of the layer formed, coating of resulting titanium dioxide platelets, without intermediate drying, with iron oxide in a wet process, drying and calcining, the layer thicknesses of the titanium dioxide layer and iron dioxide layer being adjusted such that either the stoichiometric ratio between iron oxide and titanium dioxide necessary for the formation of pseudo-brookite or ilmenite is obtained or an excess of iron oxide or titanium dioxide is present.

2. A pearlescent pigment according to claim 1, wherein the aqueous solution of a thermally hydrolyzable titanium compound is an aqueous titanium tetrachloride solution.

3. A process for the preparation of the pearlescent pigments according to claim 1, wherein the pearlescent pigments comprise iron titanate, said process comprising applying an aqueous solution of a thermally hydrolyzable titanium compound as a thin film to a continuous belt, the film thickness being adjusted such that the stoichiometric ratio between iron and titanium necessary for the formation of pseudo-brookite or ilmenite is established, solidifying the liquid film by drying, during which the titanium dioxide is developed from the solution by a chemical reaction, detaching the layer formed from the belt, suspending the resulting titanium dioxide platelets in water, without intermediate drying, and coating with iron oxide, the layer thickness being adjusted such that the stoichiometric ratio between iron and titanium necessary for the formation of pseudo-brookite or ilmenite is obtained, and the coated particles are optionally separated off from the aqueous suspension and dried and optionally calcined in an oxidizing or reducing atmosphere at not less than 500° C.

4. A process for the preparation of the pearlescent pigments according to claim 1, wherein the pigments are formed from a core of plateletlike titanium dioxide and a top layer of iron titanate, comprising applying an aqueous solution of a thermally hydrolyzable titanium compound as a thin film to a continuous belt, the film thickness being adjusted such that an excess of titanium dioxide is present for the formation of both ilmenite and pseudo-brookite, solidifying the liquid film by drying, during which the titanium dioxide is developed from the solution by a chemical reaction, detaching a layer formed from the belt, suspending a resulting titanium dioxide particles in water, without intermediate drying, and coating with iron oxide, the layer thickness being adjusted such that an excess titanium dioxide is present for the formation of both ilmenite and pseudo-brookite, and optionally the coated particles are separated off from the aqueous suspension and dried and optionally calcined in an oxidizing or reducing atmosphere at not less than 500° C.

5. A process for the preparation of the pearlescent pigments according to claim 1, wherein the pigments have three layers and a core of plateletlike titanium dioxide is followed by a layer of iron titanate and a top layer of iron oxide, comprising applying an aqueous solution of a thermally hydrolyzable titanium compound as a thin film to a continuous belt, the film thickness being adjusted such that a layer thickness of the $TiO_2$ layer of at least 40 nm results, solidifying the liquid film by drying, during which the titanium dioxide is developed from the precursor by a chemical reaction, detaching a layer formed from the belt, suspending a resulting titanium dioxide particles in water, without intermediate drying, and coating with iron oxide, the iron oxide precipitation being carried out such that a layer thickness of at least 20 nm results after the drying, and optionally separating the coated particles from the aqueous suspension and dried and optionally calcining in an oxidizing or reducing atmosphere at not less than 500° C.

6. A process according to claim 5, wherein a titanium dioxide layer is also precipitated onto the iron oxide layer, the titanium dioxide precipitation being carried out such that a layer thickness of at least 40 nm results after drying.

7. A process according to claim 3, wherein the aqueous solution of a thermally hydrolyzable titanium compound is an aqueous titanium tetrachloride solution.

8. In a coating, printing ink, plastic, cosmetic, ceramic or glass pigmented with a pigment, the improvement in the pigment is one according to claim 1.

9. A titanate-containing pearlescent pigment comprising iron titanate and optionally titanium oxide and/or iron oxide, having a planeparallel surface, a thickness tolerance of lower than 10% and a layer thickness of lower than 500 nm.

* * * * *